United States Patent
Karl et al.

(12)

(10) Patent No.: US 6,419,866 B1
(45) Date of Patent: Jul. 16, 2002

(54) PROCESS OF MAKING SYNTHETIC ABSORBABLE AUTOCLAVEABLE MONOFILAMENT FIBERS AND BRACHYTHERAPY SEED SPACERS

(75) Inventors: John J. Karl, Hopatcong; Nicholas Popadiuk, Hillsborough; Dennis D. Jamiolkowski, Long Valley; Kenneth Michael Keilman, Raritan, all of NJ (US); Saša Andjelić, New York, NY (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 09/468,463

(22) Filed: Dec. 21, 1999

(51) Int. Cl.⁷ .................. A61M 36/00; B29C 69/00; D01D 5/098; D01D 10/02
(52) U.S. Cl. .............. 264/148; 264/210.5; 264/210.8; 264/211.17; 264/235.6
(58) Field of Search ................... 264/148, 210.5, 264/210.8, 211.17, 235.6

(56) References Cited

U.S. PATENT DOCUMENTS

| 3,792,010 A |   | 2/1974  | Wasserman et al. |
|-------------|---|---------|------------------|
| 4,671,280 A | * | 6/1987  | Dorband et al. ............ 606/220 |
| 4,815,449 A |   | 3/1989  | Horowitz et al.  |
| 4,976,909 A |   | 12/1990 | Dorband et al.   |
| 5,294,395 A | * | 3/1994  | Broyer ................ 264/210.5 X |
| 5,718,716 A | * | 2/1998  | Goddard et al. ...... 264/210.8 X |
| 6,221,003 B1 | * | 4/2001 | Sierocuk et al. ............... 600/7 |

FOREIGN PATENT DOCUMENTS

EP         0830866 A2     3/1998

* cited by examiner

*Primary Examiner*—Leo B. Tentoni

(57) ABSTRACT

The present invention is directed to absorbable, autoclaveable, monofilament fibers prepared from absorbable glycolide-rich polymers, in which the fibers are oriented in the total draw ratio range 4.1 to 5.6x, and are annealed at a temperature between about 165° C. and about 185° C.; to brachytherapy seed spacers manufactured from the absorbable, autoclaveable, glycolide-rich polymers, monofilament fibers; and to methods of manufacturing such fibers and brachytherapy seed spacers.

12 Claims, No Drawings

PROCESS OF MAKING SYNTHETIC ABSORBABLE AUTOCLAVEABLE MONOFILAMENT FIBERS AND BRACHYTHERAPY SEED SPACERS

FIELD OF THE INVENTION

The present invention relates to synthetic, absorbable monofilament fibers of glycolide-based polymers, especially poly(lactide-co-glycolide) copolymers, that are useful in the fabrication of brachytherapy seed spacers in brachytherapy seed delivery systems.

BACKGROUND OF THE INVENTION

Prostatic cancer has been estimated to affect as many as one in three men. In the U.S. alone, this implies an estimated fifty-million patients who are candidates for treatment of prostatic cancer. Prior methods of treatment include surgical intervention, external radiotherapy, and other brachytherapy (interstitial radiation) techniques. A general discussion of the localized use of radiation therapy is found in Bagshaw, M. A., Kaplan, I. D. and Cox, R. C., Radiation Therapy for Localized Disease, CANCER 71: 939–952, 1993. Disadvantages associated with surgical intervention include impotence and incontinence. External radiotherapy may have deleterious effects on surrounding normal tissues (e.g., the bladder, the rectum, and the urethra). In contrast, brachytherapy diminishes complications such as impotence and incontinence, and allows a higher and more concentrated radiation dose to be delivered to the prostate gland as compared to external radiotherapy. An additional advantage of brachytherapy is that treatment can be accomplished within a matter of days as compared to weeks, greatly reducing radiation exposure of the adjacent organs.

Prostate brachytherapy can be divided into two categories, based upon the radiation level used. The first category is temporary implantation, which uses high activity sources, and the second category is permanent implantation, which uses lower activity sources. These two techniques are described in Porter, A. T. and Forman, J. D., Prostate Brachytherapy, CANCER 71: 953–958, 1993. The predominant radioactive sources used in prostate brachytherapy include iodine-125, palladium-103, gold-198, ytterbium-169, and iridium-192. Prostate brachytherapy can also be categorized based upon the method by which the radioactive material is introduced into the prostate. For example, an open or closed procedure can be performed via a suprapubic or a perineal retropubic approach.

Prostate cancer is a common cancer for men. While there are various therapies to treat this condition, one of the more successful approaches is to expose the prostate gland to radiation by implanting radioactive seeds. The seeds are implanted in rows and are carefully spaced to match the specific geometry of the patient's prostate gland and to assure adequate radiation dosages to the tissue. Current techniques to implant these seeds include loading them one at a time into the cannula of a needle-like insertion device, which may be referred to as a brachytherapy needle. Between each seed may be placed a spacer. In this procedure, a separate brachytherapy needle is loaded for each row of seeds to be implanted.

Although seed spacers may be made from a variety of materials, both absorbable and non-absorbable, there are advantages if the material is absorbable. These advantages include minimizing or eliminating any effects due to the long-term presence of the material in the body. Absorbable materials include catgut, collagen, and synthetic absorbable polymers. Catgut and collagen usually degrade by an enzymatic mechanism, as opposed to a chemical mechanism such as reaction with water, that is, hydrolysis. The preferred method of sterilization for brachytherapy seeds and spacers is steam sterilization (autoclaving). When catgut is used as a seed spacer material, the autoclaving process utilized may make the spacer soft, presumably by the plastisizing effects of the water which these materials uptake during exposure. Besides not retaining physical characteristics, catgut seed spacers also can change shape when exposed to autoclaving. Present-day synthetic absorbable materials do not uptake as much water as catgut or collagen. They do, however, degrade by a hydrolysis mechanism. It is well known that these hydrolysis reactions occur at faster rates at higher temperatures. As the preferred sterilization method for brachytherapy seeds and spacers is steam sterilization (autoclaving), it is surprising that synthetic materials known to date can effectively function in these applications. Indeed, based on the knowledge that synthetic absorbable polymers generally degrade by chemical hydrolysis, most would not even consider them for use as medical devices that would be sterilized by autoclaving.

One approach to minimizing the effects of steam sterilization on the premature degradation of seed spacers made from synthetic absorbable polymers would be to consider those synthetic absorbable polymers that are much more resistant to hydrolysis. Such a material is polylactide. This material has a much higher probability of maintaining mechanical properties required for use in brachytherapy seed delivery devices after it has been exposed to autoclaving, compared to, for instance, polyglycolide. Yet, because polylactide takes so much longer to absorb in the body, it is not generally a material of choice. The high-lactide polymer, 95/5 poly(lactide-co-glycolide), used in the production of certain long-term commercial suture materials useful in certain orthopedic surgical procedures, also takes too long to absorb in the brachytherapy procedures.

Other problems exist with certain synthetic absorbable polymers. For instance, the synthetic absorbable polymer poly(p-dioxanone), although known to retain its strength for much longer time periods than polyglycolide, is too low melting to be suitable for sterilization by autoclaving. As such, proper selection of material is an important criterion in the manufacture of monofilament fibers having properties suitable for use as brachytherapy seed spacers.

In addition to material selection, we have found that the process of manufacture is an important factor. Although injection molding appears to be an entirely suitable manufacturing process to make seed spacers, if injection molding most synthetic absorbable polymers is utilized as the manufacturing process, the spacers so produced tend to break down excessively during the sterilization process, retaining very little strength. We have found a process of making brachytherapy seed spacers from glycolide-rich synthetic absorbable polymers entailing a preferred extrusion, drawing, and annealing process to provide monofilament fibers with suitable properties which can be cut to length.

Monofilament fiber, for use in many applications, needs to be particularly straight, devoid of curves or bows, to allow proper functioning. One such application is brachytherapy seed spacers. If the seeds are curved or bowed, they may jam the applier during application of the seed/seed spacer assembly. Additionally, undesirable dimensional spacing variation may result if the seeds are curved initially, or worse yet, curve or bow irreproducibily once in the assembly, as this may initially go undetected. Since the function of brachytherapy seed spacers is to help position radioactive seeds to provide radioactivity in spatially suitable pattern, the seeds must be sufficiently dimensionally accurate and stable. Fibers made by some spinning processes are not straight after extrusion and drawing. They tend to retain some coil memory. Even after rack annealing, fibers made by some processes still can be curved due to residual coil memory.

Other various process conditions may adversely affect the properties required of the fibers for use as brachytherapy seed spacers. Upon sterilization by autoclaving, too much undesirable shrinkage in length may occur or the parts may undergo warping or bending.

Besides the "brooming" that may be experienced upon cutting fibers to length, some fabricated devices, i.e. seed spacers, also may "broom" or split during surgery under mechanical loading. Too much undesirable shrinkage in length, warping or bending upon autoclaving sterilization, or "brooming" or collapse during loading are failures that are particularly troublesome, as they occur at a point when they are difficult to detect or worse yet, during the actual surgical procedure.

It would be advantageous to develop a synthetic, absorbable monofilament fiber that both is absorbable by the body and maintains mechanical properties such that the fibers are suitable for use as brachytherapy seed spacers in brachytherapy seed delivery systems. It also would be advantageous to provide robust processes for reliably making such synthetic absorbable monofilament fibers having absorbability and mechanical strength suitable for use as brachytherapy seed spacers.

According to the present invention, a manufacturing process is provided for the production of a synthetic, absorbable, monofilament fiber suitable for the fabrication of medical devices that require autoclaving as the means of sterilization, such as seed spacers. We have discovered unexpectedly that monofilament fibers prepared from certain glycolide-rich copolymers, which fibers have been oriented in a total draw ratio of 4.1 to 5.9×, and have been annealed between about 165° C. and 185° C., can undergo a sterilizing autoclave cycle and still retain sufficient properties so as to allow their use in certain medical procedures, including brachytherapy.

Summary OF THE INVENTION

The present invention is directed towards monofilament fibers prepared from polymers containing about 80 to 100 mole percent, preferably about 85 to 100 mole percent, polymerized glycolide monomer. The glycolide homopolymer also is known as polyglycolide or as polyglycolic acid. Preferably the fibers are prepared from polymers comprising 0 to about 15 mole percent polymerized lactide monomer and 100 to about 85 mole percent polymerized glycolide monomer, i.e. poly(lactide-co-glycolide). Most preferably, the polymers comprise about 10 mole percent polymerized lactide monomer and about 90 mole percent polymerized glycolide monomer. The fibers are oriented at a total draw ratio range of 4.1 to 5.9×, and are annealed at a temperature between about 165° C. and about 185° C. Such fibers are absorbable by the body and are capable of undergoing an autoclave process used to sterilize brachytherapy seed spacers, while retaining mechanical properties required for use as brachytherapy seed spacers in brachytherapy seed delivery devices. The invention also is directed to brachytherapy seed spacers prepared from the monofilament fibers. The invention also is directed to methods of manufacturing such fibers and brachytherapy seed spacers.

DETAILED DESCRIPTION OF THE INVENTION

Polymers used in preparation of the monofilament fibers of the present invention must be absorbable by the body when used as brachytherapy seed spacers. By absorbable, it is meant that the material does not simply dissolve away from the implant site, but is converted to lower molecular weight species that are removed from the site and usually from the body by biological means. The conversion to lower molecular weight species, in the case of most synthetic absorbable polymers, is effected by chain cleavage by chemical hydrolysis. In the case of brachytherapy seed spacers, it is preferable to have the devices "cleared" in no more than about three or four months after the procedure.

In addition to being absorbable, the fibers prepared from the polymers must possess certain mechanical properties in order to be useful as brachytherapy seed spacers. In particular, the column strength of the fiber, at a minimum, must be effective to prevent the fiber from splitting or brooming upon cutting to length in the manufacture of seed spacers. Preferably, the column strength of the fiber, and subsequently the seed spacer, will be at least 3.5 pounds after autoclaving. The surface of the fiber must be sufficiently smooth for use as brachytherapy seed spacers. In addition, the fiber must be dimensionally stable and autoclaveable, meaning that the fiber retains shape and dimension effective for use as a seed spacer when subjected to an autoclaving process suitable for sterilization of seed spacers and practiced in the hospital environment.

As mentioned earlier, polylactide homopolymers have been found to provide adequate mechanical properties, but are deficient in that they take too long to be absorbed by the body. The melting temperature of poly(p-dioxanone) polymer is too low to survive the autoclave process. The synthetic absorbable polymers containing polymerized glycolide that have glass transition temperatures below room temperature and that have found commercial utility as monofilament sutures, such as the segmented copolymers of glycolide and caprolactone, generally do not have the mechanical properties needed to function as seed spacers after being sterilized by autoclaving. We have thus found that not all synthetic absorbable polymers function equally as seed spacer materials.

It has been unexpectedly discovered that monofilament fibers prepared from glycolide-rich polymers containing about 85 to 100 mole percent polymerized glycolide, preferably made from poly(lactide-co-glycolide), comprising from 0/100 to about 15/85 mole percent lactide/ glycolide, and most preferably, 10/90 poly(lactide-co-glycolide), in which the fibers have been oriented in the total draw ratio range of 4.1 to 5.9× and in which the fibers have been annealed at a temperature between about 165° to about 185° C., may be used to reliably fabricate absorbable, autoclaveable brachytherapy seed spacers for use in brachytherapy seed delivery devices. Despite being absorbable in the body by virtue of a relatively facile reaction rate with water; that is, relatively facile chemical hydrolysis, seed spacers of the subject invention can withstand exposure to water (steam) at the high temperatures, and for the time periods necessary to sterilize by a conventional autoclaving cycle.

Polymers used to prepare fibers according to the present invention generally are prepared from 100 to about 80 mole percent glycolide monomer and from 0 to about 20 mole percent of a copolymerizable comonomer. Exemplary comonomers may be selected from the group consisting of L(−)-lactide, D(+)-lactide, meso-lactide, p-dioxanone, trimethylene carbonate and epsilon-caprolactone. If less than about 80 mole percent glycolide is used, the fibers manufactured therefrom will not possess sufficient mechanical properties required for use in brachytherapy seed spacers. A preferred comonomer is lactide, especially at about a 10 mole percent level. Other sequences may be incorporated in the polymer, for instance, by adding an alpha,omega-dihydroxy compound at the start of the polymerization.

Generally, the polymers of the present invention have molecular weights, prior to extrusion, corresponding to inherent viscosity (IV) values of about 1.0 to about 2.5 dL/g, as measured in hexafluroisopropanol (HFIP) at 25° C., at a concentration of 0.1 g/dL. It is preferable that the IV values of the resins range from 1.2 to 2.1 dL/g, more preferably between 1.3 and 2.0 dL/g, and most preferably between 1.4 and 1.7 dL/g. It should be understood that if the molecular weight of the polymer were too low, it would be very difficult to orient the fiber in the draw ratio range required according to the present invention. If the molecular weight is too high, difficulty in conveying the molten resin during extrusion may result.

In a process for making monofilament fibers disclosed in U.S. Pat. No. 4,671,280, entitled Surgical Fastening Device And Method for Manufacture, in the name of Dorband et al., the contents of which are hereby incorporated by reference in their entirety, the fibers prepared from polymers comprising greater than 80 mole percent polymerized glycolide are oriented in a total draw ratio of 7.4× and annealed at 135° C. On the other hand, fibers according to the present invention must be oriented in a total draw ratio of 4.1 to 5.9×, more preferably from about 4.5 to about 5.5. When the total draw ratio is too low, the fibers exhibit insufficient column strength retention after autoclaving when used as a brachytherapy seed spacer. When the total draw ratio is too high, the surface of the resulting fiber may be too rough for use as a seed spacer, and/or the ends of the fibers may easily split apart, or "broom", upon cutting to length or during mechanical loading as occurs during introduction of a seed/seed spacer assembly in surgery.

In order for the process used to manufacture fibers according to the present invention to be robust, it should consistently provide fiber having the mechanical properties required for use in brachytherapy seed spacers, particularly dimensional stability and surface smoothness. We surprisingly have discovered that when the extruded, oriented monofilament fibers comprising 100 to about 80 mole percent polymerized glycolide are oriented to a total draw ratio between 4.1 to 5.9× and annealed at a temperature between about 165° C. and about 185° C., fibers that exhibit required dimensional stability and surface smoothness consistently are provided. When the annealing temperature is less than about 165° C., e.g. about 155° C., the fibers often exhibit insufficient mechanical properties such as bowing. More preferably, the fibers are annealed between about 170° C. and about 180° C. Even more preferably, the fibers are annealed at about 175° C.

Upon sterilization by autoclaving, too much undesirable shrinkage in length may occur, or parts may undergo warping or bending. Besides the "brooming" that may be experienced upon cutting fibers to length, some fabricated devices, i.e. seed spacers, also may "broom" or split during surgery under mechanical loading. Fibers and spacers that exhibit too much undesirable shrinkage in length, warping or bending upon autoclaving sterilization, or "brooming", or collapse during loading are considered ineffective for use in brachtherapy.

By "autoclaveable", it is meant that the fiber, in the form of a seed spacer, maintains at least 3.5 lbs of column strength and does not warp or bend during the autoclave cycle, thus preventing its use as a brachytherapy seed spacer.

Although seed spacer diameters between about 30 and 40 mils are particularly advantageous, it is to be understood that the diameter of monofilament fibers of the subject invention can be as low as about 20 mils and as high as about 60 mils or greater. Generally the cross-section of the fibers will be circular, but other shapes may be used to advantage. In the case of non-circular cross-sections, corresponding cross-sectional areas will dominate.

Processes for making the glycolide-rich fibers and brachytherapy seed spacers of the present invention are set forth herein.

EXAMPLE 1

Polymers and Polymerization

Generally the polymers of the present invention have molecular weights, prior to extrusion, corresponding to inherent viscosity (IV) values of about 1.0 to about 2.5 dL/g, as measured in hexafluroisopropanol (HFIP) at 25° C. at a concentration of 0.1 g/dL. It is preferable that the IV values of the resins range from 1.2 to 2.1, more preferably between 1.3 and 2.0, and most preferably between 1.4 and 1.7 dL/g. Preferably the polymer is 10/90 molar ratio poly(lactide-co-glycolide). In those cases in which the polymerized glycolide content is very high, for instance 97 to 100 mole percent, the resins may be very difficult to dissolve, even in HFIP, if they have been allowed to crystallize significantly. Inherent viscosity measurements may then need to be made after first melting a sample of the (dried) resin and then quickly quenching it to avoid crystallization. Samples, so treated, usually can be dissolved in HFIP of IV determinations.

The polymers of the present invention generally can be made by the ring opening polymerization of the glycolide monomer, and in the case of certain copolymers, monomers selected from the group consisting of L(−)-lactide, D(+)-lactide, meso-lactide, p-dioxanone, trimethylene carbonate and epsilon-caprolactone. These other monomers may be used in any combination with glycolide monomer, provided that the formed polymer resin suitable for extrusion contains at least 80 mole percent glycolide. The polymerizations can be conducted, by placing the monomer or monomers, a catalyst such as stannous octoate, and an initiator such as dodecanol, in a suitable reaction vessel, purging to provide an inert atmosphere, and heating at a sufficient temperature and time. The resulting polymer can be ground or pelletized to produce resin suitable for "drying", that is, the removal of unreacted monomers. Other sequences may be incorporated in the polymer for instance, by adding an alpha,omega-dihydroxy compound at the start of the polymerization. The final resin should contain at least 85 mole percent glycolide sequences.

Extrusion/Orientation

Monofilament fibers of the present invention were extruded using a one-inch horizontal extruder, with water quench temperatures ranging from 20° C. to 40° C. (See Table 1). Typical extruder temperatures ranged from 225° C. to 250° C. although depending on the resin, temperatures may range from about 200° C. to about 265° C. The diameter of the extruder die was changed dependent on the amount of orientation provided to the filament in the next stage. In the experiments described, die diameters ranged from 200 to 220 mils. The higher the draw ratio employed, the larger the die diameter was selected so as to help keep the oriented fiber diameter fairly constant. By way of example, for a final oriented fiber diameter of 35 mils, suitable die diameters may be as low as 140 mils to as high as about 255 mils.

The filament was oriented in stages between godets with in-line ovens located between the godets. The draw ratio between the first and second set of godet rolls is between 4.5 and 5.0×, with oven temperature between 50° C. and 75° C. The third stage has an additional draw of between 1.01 to 1.2, with oven temperatures between 50° C. and 75° C.

TABLE 1

| Quench Temp (° C.) | Height (in.) | Godet 1 Speed/Temp (Fpm/° F.) | Oven 1 Temp (° C.) | Godet 2 Speed (Fpm) | Oven 2 Temp (° C.) | Godet 3 Speed (Fpm) | Fiber Diameter (Mils) | Tensile (Lbs) | Elong At Break (%) |
|---|---|---|---|---|---|---|---|---|---|
| 20 | 0.25 | 20 | — | — | — | — | 29.6 | 7.3 | — |
| 20 | 0.25 | 20/127 | RT | 30 | NA | NA | 29.8 | 11.1 | 209 |
| 20 | 0.25 | 20/145 | RT | 66 | NA | NA | 28.3 | 37.7 | 88.8 |
| 20 | 0.25 | 20/125 | RT | 68 | NA | NA | 27.8 | 29.7 | 54.5 |
| 20 | 0.25 | 20/137 | RT | 100 | NA | NA | 28.7 | 20.4 | 32.5 |
| 20 | 0.5 | 20/150 | RT | 120 | NA | NA | 29.8 | 21.1 | 10.7 |
| 20 | 0.5 | 20/147 | RT | 100 | NA | NA | 32.9 | 44.8 | 33.3 |
| 20 | 0.5 | 20/145 | RT | 100 | NA | NA | 34.7 | 41.4 | 31.2 |
| 20 | 0.5 | 20/148 | RT | 120 | NA | NA | 31.9 | 28.4 | 23.3 |
| 20 | 3.5 | 20/131 | 160 | 100 | NA | NA | 36.2 | 90.7 | 50.1 |
| 20 | 2.5 | 20/131 | 160 | 100 | NA | NA | 37.1 | 89.9 | 51.2 |
| 20 | 3.5 | 20/131 | 165 | 100 | NA | NA | 37.0 | 91.8 | 53.2 |
| 20 | 1.0 | 20/131 | 160 | 100 | NA | NA | 35.8 | 56.7 | 36.7 |
| 20 | 5.0 | 20/131 | 160 | 100 | NA | NA | 36.7 | 89.0 | 52.7 |
| 20 | 3.5 | 20/131 | 165 | 100 | 170 | 110 | 35.3 | 89.1 | 44.0 |
| 20 | 3.5 | 15/RT | 165 | 55 | 165 | 75 | 36.6 | 105.9 | 44.0 |
| 40 | 3.5 | 15/RT | 165 | 55 | 165 | 75 | 35.5 | 111.1 | 41.3 |
| 40 | 2.0 | 15/RT | 165 | 55 | 165 | 75 | 35.5 | 109.5 | 40.7 |
| 40 | 5.0 | 15/RT | 165 | 55 | 165 | 75 | 36.2 | 109.0 | 42.4 |
| 40 | 3.5 | 15/RT | 165 | 55 | 165 | 75 | 36.4 | 105.4 | 42.2 |
| 40 | 3.5 | 15/RT | 165 | 55 | 165 | 75 | 36.0 | 100.6 | 44.1 |
| 40 | 3.5 | 15/RT | 180 | 55 | 180 | 75 | 36.2 | 80.8 | 53.5 |
| 40 | 3.5 | 15/RT | 165 | 55 | 165 | 75 | 35.8 | 98.6 | 43.5 |

RT = Room Temperature

Draw ratios between godets can be calculated by dividing the linear speed of the later godet by that of the earlier godet, provided there is no significant slippage of the fiber on the godet rolls. That is, with godets 1, 2, and 3 running at 15, 55, 75 feet per minute, respectively, the draw ratio between godets 1 and 2 is 55/15 or 3.67x, between godets 2 and 3 is 75/55 or 1.36. The total draw ratio may be calculated by multiplying the respective individual draw ratios, e.g. 3.67× 1.36=5.0 for the above example. If there is slippage on the godet rolls, fiber speeds will be used to calaculate draw ratio. In the case a fiber with a circular cross-section, draw ratios can also be calculated from diameter measurements of the fiber before and after a particular drawing stage: the square root of the ratio of initial diameter to that of the final diameter is the draw ratio. In general, for fibers with circular or non-circular cross-sections, the ratio of the initial cross-sectional area to that of the final cross-sectional area is the draw ratio.

ANNEALING

Once the extruded monofilament fiber is oriented, it may be stored on a spool. It is then wound onto a standard rack-with minimum tension, for instance approximately one pound. Racks approximately 36 inches in length are suitable. The filament tension is controlled during winding of the fiber around the rack, such that there may be about 5% change in length after annealing. The wound fiber is placed in the oven and the oven is purged with nitrogen. While the annealing oven may be heated at a rate of about 1° C. per minute, other heating rates may be used. Alternately, the annealing cycle may include incremental hold times at elevated temperatures prior to reaching the final temperature between about 165° C. and 185° C. For instance, an incremental hold time of 1 hour at 75° C. can be used prior to heating to the final temperature. After the heat cycle, the material is cooled to ambient temperature, manually cut off the rack into 30-inch strands and stored in a vacuum chamber until it is ready to be cut into the final dimensions.

Column strength tests were performed on fibers in the following manner: The test equipment was set up to have a compression type load cell of at least 100 lbs. A stainless steel tube that has an inside diameter that accommodates a stylet and needle is used to compress the cut fiber (spacer). The tube is clamped vertically such that the needle pushes the spacer in a downward position. Once the position is set for the equipment, the gauge length is "zeroed" to ensure that the stylet and pusher is not overrun. The crosshead speed is set at 0.5 inch/second. The maximum load and displacement at maximum load are recorded.

The fibers described in Table 2 were annealed at 145° C. prior to autoclaving and then evaluated for column strength after autoclaving as set forth above. Some of the samples exhibited unacceptable column strength after annealing or unacceptably rough surface.

TABLE 2

| Sample ID | Godet 1 Speed (fpm) | Godet 2 Speed/ Temp (fpm/° C.) | Oven 1 Temp (° C.) | Godet 3 Speed (fpm) | Oven 2 Temp (° C.) | Godet 4 Speed (fpm) | Total Draw Ratio | Column Strength Performance |
|---|---|---|---|---|---|---|---|---|
| INDM XX1-1 | 20.0 | NA | NA | NA | NA | NA | 1.0 | Disintegrated during autoclaving |

TABLE 2-continued

| Sample ID | Godet 1 Speed (fpm) | Godet 2 Speed/ Temp (fpm/° C.) | Oven 1 Temp (° C.) | Godet 3 Speed (fpm) | Oven 2 Temp (° C.) | Godet 4 Speed (fpm) | Total Draw Ratio | Column Strength Performance |
|---|---|---|---|---|---|---|---|---|
| INDM XX2-2 | 20.0 | 20/42 | NA | 30 | NA | NA | 1.5 | Disintegrated during autoclaving |
| INDM XX3-1 | 20.0 | 20/42 | NA | 68 | NA | NA | 3.4 | Disintegrated during autoclaving |
| INDM XX11-13 | 14.76 | 20/50 | 50 | 62.4 | 50 | 72.5 | 4.8 | Good - meets CS requirements |
| INDM XX4-1 | 20.0 | 20/47 | NA | 100 | NA | NA | 5.0 | Good - CS after Autoclaving = 16.16 lbs |
| INDM XX7-1 | 20.0 | 20/55 | 54 | 98.4 | NA | 100 | 5.0 | Good - CS after Autoclaving = 20.39 lbs |
| INDM XX7-5 | 20.0 | 20/55 | 65 | 98 | NA | 100 | 5.0 | Good - CS after Autoclaving = 19.27 lbs |
| INDM XX8-5 | 20.0 | 20/52 | 72 | 108 | NA | 110 | 5.5 | Good - CS after Autoclaving = 28.99 lbs |
| INDM XX6-5 | 20.0 | 20/53 | NA | 120 | NA | NA | 6.0 | Not Tested Because Unacceptably Rough Surface |

Annealed strands were evaluated against performance criteria such as straightness, the ability to be cut easily without splitting or brooming and column strength after autoclaving. Results are presented in Table 3. It is noted that fibers annealed at about 155° C. or less exhibited inconsistent performance results. Sample 2a, annealed at 145° C., failed because it did not meet the straightness criterion, i.e. it exhibited bowing. Samples C, D, and G in Table 3, annealed at 155° C., also failed because they did not meet the straightness criterion.

TABLE 3

| Sample | Preheat Temp (° C.) | Duration Time (hrs) | Oven Set Temp (° C.) | Duration Time (hrs) | Straightness | CS Before Autoclaving | CS After Autoclaving |
|---|---|---|---|---|---|---|---|
| 1 | 75 | 1 | 145 | 6 | Good | Good | Good |
| 2 | — | — | 145 | 6 | Good | Good | Good |
| 2a | — | — | 145 | 6 | Failed - Bowed | CS not determined because sample failed "Straightness" | |
| 3 | 75 | 1 | 155 | 6 | Good | Good | Good |
| 4 | — | — | 155 | 6 | Good | Good | Good |
| A | — | — | 155 | 6 | Good | 13.86 | 12.24 |
| B | — | — | 155 | 6 | Slight Bow Fair | 17.17 | 15.83 |
| C | — | — | 155 | 6 | Failed - Bowed | CS not determined because sample failed "Straightness" | |
| D | — | — | 155 | 6 | Failed - Bowed | CS not determined because sample failed "Straightness" | |
| G | — | — | 155 | 6 | Failed - Bowed | CS not determined because sample failed "Straightness" | |
| E | — | — | 175 | 6 | Good | 22.93 | 21.89 |
| F | — | — | 175 | 6 | Good | 20.36 | 18.23 |

We have unexpectedly discovered that monofilament fibers prepared from glycolide—rich polymers described herein above and that have been oriented in a total draw ratio of 4.1 to 5.9× and that have been annealed at a temperature between about 165° to about 185° C., may be used to reliably fabricate absorbable, autoclaveable brachytherapy seed spacers for use in brachytherapy seed delivery devices.

Utilizing the Fibers Described above, Brachytherapy Seed Spacers were Prepared as Follows:

Cutting:

Fibers of the present invention may be cut in any manner that will provide the dimensional requirements required for use as brachytherapy seed spacers. This may include mechanical or thermal means. An in-line cutting mechanism provides an economically advantageous way of cutting. Cutting must be conducted so that it does not "mushroom", crush, broom, or delaminate the fiber. Manual cutting is possible and may be accomplished with a "razor blade" or a "paper cutter" type of cutting mechanism. After cutting, the fibers preferably are stored in a water-free environment, such as a "nitrogen box" or a vacuum chamber. Simple cutting mechanisms provide the advantage of capital cost avoidance regarding complex equipment. The fibers of the subject invention have additional advantage in that they can be cut by simply means without "mushrooming", crushing, brooming, or delaminating, to allow their use as brachytherapy seed spacers.

Sterilization by Autoclaving

Different types of commercial autoclaving sterilizers are available. Two major classes are known by some as the "pre-vacuum" type and the "gravity-displacement" type. The pre-vacuum type of sterilizer depends upon one or more pressure and vacuum excursions at the beginning of the cycle to remove air. This method of operation results in shorter cycle times for wrapped items because of the rapid removal of air from the chamber (and the "load" or items to be sterilized) by a vacuum system and because of a usually higher operating temperature (for instance 132° C. to 135° C., or 250° F. to 254° F.). Typical operating parameters for a pre-vacuum type of sterilizer are 3 to 4 minutes at 132° C. to 135° C. A gravity-displacement type of sterilizer is one in which incoming steam displaces residual air through a port or drain in or near the bottom of the sterilizer chamber. Typical operating parameters for a gravity-displacement type of sterilizer include 15 to 30 minutes at 121 to 123° C.

Four types of sterilization cycles were used to sterilize the samples: (1) pre-vacuum at 275° F. (135° C.) for 10 minutes; (2) gravity-displacement at 275° F. (135° C.) for gravity-displacement at 275° F. (135° C.) for 25 minutes; (4) gravity-displacement at 254° F. (123.3° C.) for 30 minutes.

EXAMPLE 2

Another method of manufacturing a dimensionally stable absorbable spacer according to the present invention includes the following steps. Using a typical horizontal extruder, such as a one-inch 24:1 extruder, pellets of the polymer are melted and then extruded through a die to form monofilaments. The filaments then are quenched, for instance, using a heated water bath. More particularly, the horizontal extruder includes a number of zones, for instance, three zones, all which may be set independently at temperatures of between about 200° C. and about 260° C., and preferably between about 225° C. and 250° C. As the polymer pellets are passed through the three zones, they melt and the melted polymer is forced through a flange which is heated to a temperature of between about 210° C. and 265° C. and preferably between about 230° C. and 255° C. After passing through the heated flange, the melted polymer enters a pump, which has a temperature of between about 210° C. and 265° C. and preferably between about 232° C. and 255° C. Finally, the melted polymer is forced through a die having a predetermined diameter of, for example 0.22 inch. The polymer then forms a long rod, which is suspended in air for approximately 2 to 4 inches and quenched in a tank of water having a temperature of approximately 30° C. to 40° C., thus completing the extrusion process. Immediately following extrusion, or alternately after some time has passed, the filaments may be oriented to about 5:1 draw ratio by stretching them between heated godet rolls or by stretching them between (optionally heated) godet rolls providing (additional) heating means such as can be achieved with in-line ovens. It is clear to those familiar with fiber manufacture that different means of stretching a fiber to achieve a particular draw ratio are available. In particular, the extruded rod may be oriented by winding it around a first roller, which is turning at a rate of approximately 4 to 6 meters per minute, which pulls the extruded rod out of the bath. The extruded rod may then be wound around a second roll that turns at a rate of 4 to 6 meters per minute. After passing around the second roll, the extruded rod may be passed through a first oven that is set at a temperature of approximately 50° C. to 55° C. After passing through the first oven, the extruded rod may be passed around a third roll that is turning at a rate of between 17 and 21 meters per minute. After passing around the third roll, the extruded rod is passed through a second oven that is set at a temperature of between 50° C. to 55° C. After passing through the second oven, the extruded rod is wound around a fourth roll that is turning at a rate of between 24 and 31.5 meters per minute. Prior to cutting and sterilizing, the rod must be annealed between about 165° C. and 185° C.

It will be recognized that an absorbable, dimensionally stable, autoclaveable seed spacer according to the present invention may be modified to include certain types of medication which may be absorbed as the spacer is absorbed. Such medications might include, for example, anti-inflammatory, anti-cancer or certain sustained-release drugs. A seed spacer according to the present invention further may include markers or other materials adapted to make the spacer visible to ultrasound or x-ray.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that the invention be limited only by the spirit and scope of the appended claims.

We claim:

1. A process for the manufacture of a monofilament fiber, comprising the steps of:

extruding a polymer comprising 100 to about 80 mole percent polymerized glycolide to form a monofilament fiber, orienting the extruded monofilament fiber to a total draw ratio of 4.1 to 5.9×; and annealing the oriented monofilament fiber at a temperature of about 165° to about 185° C.

2. The process of claim 1 wherein the polymer comprises up to about 20 mole percent polymerized monomer selected from the group consisting of L(−)-lactide, D(+)-lactide, meso-lactide, p-dioxanone, trimethylene carbonate and epsilon-caprolactone.

3. The process of claim 2 wherein the polymer comprises about 10 mole percent polymerized lactide and about 90 mole percent polymerized glycolide.

4. The process of claim 1 wherein the total draw ratio is about 4.5 to about 5.5×.

5. The process of claim 1 wherein the monofilament fiber is annealed at a temperature of about 170° C. to about 180° C.

6. The process of claim 4 wherein the monofilament fiber is annealed at a temperature of about 170° C. to about 180° C.

7. A process for the manufacture of a brachytherapy seed spacer, comprising the steps of:

extruding a polymer comprising 100 to about 80 mole percent polymerized glycolide to prepare a monofilament fiber, orienting the extruded monofilament fiber to a total draw ratio of 4.1 to 5.9×, annealing the oriented monofilament fiber at a temperature from about 165° to about 185° C.; and cutting the annealed, oriented monofilament fiber to a predetermined dimension effective for use as the brachytherapy seed spacer.

8. The process of claim 7 wherein the polymer comprises up to about 20 mole percent polymerized monomer selected from the group consisting of L(−)-lactide, D(+)-lactide, meso-lactide, p-dioxanone, trimethylene carbonate and epsilon-caprolactone.

9. The process of claim 8 wherein the polymer comprises about 10 mole percent polymerized lactide and about 90 mole percent polymerized glycolide.

10. The process of claim 7 wherein the total draw ratio is about 4.5 to about 5.5×.

11. The process of claim 7 wherein the monofilament fiber is annealed at a temperature from about 170° C. to about 180° C.

12. The process of claim 10 wherein the monofilament fiber is annealed at a temperature from about 170° C. to about 180° C.

* * * * *